US012614320B2

(12) United States Patent
Leong et al.

(10) Patent No.: US 12,614,320 B2
(45) Date of Patent: *Apr. 28, 2026

(54) VISUALIZATION TOOLS FOR DIGITAL PCR DATA

(71) Applicant: LIFE TECHNOLOGIES CORPORATION, Carlsbad, CA (US)

(72) Inventors: Harrison Leong, San Francisco, CA (US); Nivedita Sumi Majumdar, San Bruno, CA (US); Jeffrey A. Marks, Mountain View, CA (US); Theodore E. Straub, Lexington, MA (US); Ryan J. Talbot, Stamford, CT (US); Kevin S. Bodner, Belmont, CA (US); David Hoard, Escondido, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/861,854

(22) Filed: Jul. 11, 2022

(65) Prior Publication Data

US 2023/0022224 A1     Jan. 26, 2023

Related U.S. Application Data

(63) Continuation of application No. 16/937,634, filed on Jul. 24, 2020, now Pat. No. 11,417,037, which is a
(Continued)

(51) Int. Cl.
*G06T 11/20* (2006.01)
*G16B 45/00* (2019.01)

(52) U.S. Cl.
CPC .......... *G06T 11/206* (2013.01); *G06T 11/203* (2013.01); *G16B 45/00* (2019.02)

(58) Field of Classification Search
CPC ..... G06T 11/203; G06T 11/206; G16B 25/20; G16B 45/00
See application file for complete search history.

(56) References Cited

U.S. PATENT DOCUMENTS 8,572,506 B2    10/2013    Janaway et al.
10,726,589 B2     7/2020    Leong et al.
(Continued)

FOREIGN PATENT DOCUMENTS

WO        2011/127454 A2    10/2011

OTHER PUBLICATIONS

NPL: Digital PCR Analysis Software version 3, Aug. 6, 2010 (Year: 2010).*
(Continued)

*Primary Examiner* — Ming Wu
(74) *Attorney, Agent, or Firm* — Jones Burke, PLLC

(57) ABSTRACT

A method comprises displaying, on a graphical user interface (GUI), a first data visualization comprising a positional representation of a plurality of reaction sites from at least a portion of a substrate, wherein the positional representation of the first data visualization simultaneously indicates relative data quality of the plurality of reaction sites; and altering the first data visualization displayed on the GUI to a second data visualization, the second data visualization comprising the positional representation of the plurality of reaction sites from the at least the portion of the substrate, wherein the positional representation of the second data visualization simultaneously indicates relative data quality of the plurality of reaction sites from at least the portion of the substrate based on a comparison of the data quality values of the plurality of reaction sites an adjusted quality value threshold.

19 Claims, 12 Drawing Sheets

Related U.S. Application Data continuation of application No. 14/441,500, filed as application No. PCT/US2013/068984 on Nov. 7, 2013, now Pat. No. 10,726,589.

(60) Provisional application No. 61/803,010, filed on Mar. 18, 2013, provisional application No. 61/723,732, filed on Nov. 7, 2012.

(56) References Cited

U.S. PATENT DOCUMENTS

| | | | |
|---|---|---|---|
| 10,777,303 | B2 | 9/2020 | Majumdar |
| 2002/0067358 | A1 | 6/2002 | Casari et al. |
| 2002/0165674 | A1 | 11/2002 | Bassett, Jr. et al. |
| 2004/0003601 | A1 | 1/2004 | Dube |
| 2004/0012633 | A1 | 1/2004 | Helt |
| 2004/0033601 | A1 | 2/2004 | Davidson |
| 2004/0138821 | A1 | 7/2004 | Chiles et al. |
| 2005/0019792 | A1 | 1/2005 | McBride et al. |
| 2005/0119534 | A1 | 6/2005 | Trost et al. |
| 2005/0123971 | A1 | 6/2005 | Di et al. |
| 2006/0015291 | A1 | 1/2006 | Parks et al. |
| 2007/0147685 | A1* | 6/2007 | Ericson .................. G06F 18/40 |
| | | | 382/190 |
| 2007/0255506 | A1 | 11/2007 | Lobban et al. |
| 2008/0154512 | A1 | 6/2008 | Leong |
| 2008/0168151 | A1 | 7/2008 | Fuchs et al. |
| 2009/0239308 | A1 | 9/2009 | Dube et al. |
| 2010/0070904 | A1* | 3/2010 | Zigon ................. G06V 10/7625 |
| | | | 715/854 |
| 2010/0191678 | A1 | 7/2010 | Steed et al. |
| 2011/0191343 | A1 | 8/2011 | Heaton et al. |
| 2011/0250597 | A1 | 10/2011 | Larson et al. |
| 2011/0252353 | A1 | 10/2011 | Janaway et al. |
| 2012/0078601 | A1 | 3/2012 | Avinash et al. |
| 2012/0089917 | A1 | 4/2012 | Kwahk et al. |
| 2012/0100544 | A1* | 4/2012 | Hart ..................... C12Q 1/6851 |
| | | | 536/24.33 |
| 2012/0171672 | A1 | 7/2012 | Barken et al. |
| 2012/0257671 | A1* | 10/2012 | Brockmann ..... H04N 21/64753 |
| | | | 375/E7.126 |
| 2014/0087386 | A1 | 3/2014 | Chiu et al. |
| 2014/0372953 | A1 | 12/2014 | Laurance |
| 2015/0247190 | A1 | 9/2015 | Ismagilov et al. |
| 2016/0063181 | A1 | 3/2016 | Subramaniam et al. |
| 2017/0002400 | A1 | 1/2017 | Hutchison et al. |
| 2018/0225415 | A1 | 8/2018 | Majumdar |
| 2019/0330683 | A1 | 10/2019 | Link et al. |
| 2024/0132939 | A1 | 4/2024 | Larson et al. |

OTHER PUBLICATIONS

Digital PCR Analysis Software version 3, Aug. 6, 2010 (Year: 2010).*

DPlot Graph Software for Scientists and Engineers, Oct. 7, 2011.

Belder et al., "Surface modification in microchip electrophoresis", Electrophoresis 2003, 24, 3595-3606.

Digital PCR Analysis Software version 3 User Guide, Aug. 6, 2010, 95 pages.

Bio-Rad: "Droplet Digital" PCR Applications Guide, Feb. 1, 2010.

European Search Report issued in corresponding European Application No. 21212404.4, dated Mar. 21, 2022.

CN Office Action issued in corresponding Chinese Application No. 201380069424.7 issued on Apr. 13, 2020.

Chinese Supplementary Search Report issued in Chinese Application No. 2013800694247, dated Jul. 15, 2019.

European Communication issued in Application No. 13 799 705.2, dated Jan. 31, 2019.

"Applied Biosystems StepOne and StepOnePlus Real-Time PCR Systems for Genotyping Experiments", Getting Started Guide, Jun. 2010, 1-156.

"Digital PCR Analysis Software version 3", Fluidigm User Guide, 2011, 1-91.

International Preliminary Report on Patentability and Written Opinion for Application No. PCT/US2013/068984, mailed May 21, 2015, 15 pages.

International Search Report and Written Opinion of the ISA for Int'l Application No. PCT/US2013/068984, dated Jun. 12, 2014.

Whale, Alexandra S. et al., "Comparison of Microfluidic Digital PCR and Conventional Quantitative PCR for Measuring Copy Number Variation", Nucleic Acids Research, vol. 40, No. 11, e82, Feb. 1-9, 2012.

Zhong, Qun et al., "Multiplex Digital PCR: breaking the one target per color barrier of quantitative PCR", Lab on a Chip, vol. 11, 2011, 2167-2174.

* cited by examiner

VISUALIZATION TOOLS FOR DIGITAL PCR DATA

CROSS-REFERENCE TO RELATED APPLICATIONS

This application is a continuation of U.S. application Ser. No. 16/937,634, filed Jul. 24, 2020, which is a continuation of U.S. application Ser. No. 14/441,500, filed May 7, 2015 (now U.S. Pat. No. 10,726,589), which is a national stage of U.S. Application No. PCT/US2013/068984, filed Nov. 7, 2013, which claims the benefit of U.S. Application No. 61/803,010, filed Mar. 18, 2013, and U.S. Application No. 61/723,732, filed Nov. 7, 2012, which are all incorporated by reference herein in their entireties.

BACKGROUND

Systems for biological and biochemical reactions have been used to monitor, measure, and/or analyze such reactions in real time. Such systems are commonly used in sequencing, genotyping, polymerase chain reaction (PCR), and other biochemical reactions to monitor the progress and provide quantitative data.

Currently, there is an increasing demand to provide greater numbers of reactions per test or experiment have resulted in instruments that are able to conduct ever higher numbers of reactions simultaneously. The increase in the number sample sites in a test or experiment has led to microtiter plates and other sample formats that provide ever smaller sample volumes. In addition, techniques such as digital PCR (dPCR) have increased the demand for smaller sample volumes that contain either zero or one target nucleotide sequence in all or the majority of a large number of test samples.

Digital PCR may be used to detect and quantify the concentration of rare alleles, to provide absolute quantitation of nucleic acid samples, and to measure low fold-changes in nucleic acid concentration. Generally, increasing the number of replicates increases the accuracy and reproducibility of dPCR results.

In dPCR, a solution containing a relatively small number of a target polynucleotide or nucleotide sequence may be subdivided into a large number of small test samples, such that each sample generally contains either one molecule of the target nucleotide sequence or none of the target nucleotide sequence. When the samples are subsequently thermally cycled in a PCR protocol, procedure, or experiment, the samples containing the target nucleotide sequence are amplified and produce a positive detection signal, while the samples containing no target nucleotide sequence are not amplified and produce no detection signal.

For further analysis, the immense number of data points the data collected from a dPCR experiment is challenging to organize and visualize in a manner that is useful to a user.

SUMMARY

In one exemplary embodiment, a method for generating a data visualization is provided. The method includes displaying a representation of a portion of detected data from a substrate to a user. The method further includes generating a data quality value for the portion of detected data and displaying, along with the representation of the portion of detected data, an indication of data quality value for the portion of detected data. The method further includes selecting, by the user, a quality value threshold, and displaying an adjusted indication of data quality value for the portion of detected data meeting the quality value threshold.

In another exemplary embodiment, a method for calculating a result for a biological analysis is provided. The method includes displaying to a user a scatter plot of emission data from a plurality of reaction sites and determining a classification for each data point. The method further includes receiving a selection of a data point to change the determined classification to a second classification. The method includes calculating a result based on a number of data points in each classification. In some embodiments, the result is a concentration of a target molecule. According to various embodiments, classifications may include: positive reaction, negative reaction, FAM, VIC, FAM and VIC, no amplification, empty, and undetermined.

DETAILED DESCRIPTION

To provide a more thorough understanding of the present invention, the following description sets forth numerous specific details, such as specific configurations, parameters, examples, and the like. It should be recognized, however, that such description is not intended as a limitation on the scope of the present invention, but is intended to provide a better description of the exemplary embodiments.

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on computer-readable media. Some other processes can be implemented using analog circuitry, as is well known to one of ordinary skill in the art. Additionally, memory or other storage, as well as communication components, may be employed in embodiments of the invention.

Figure 1:
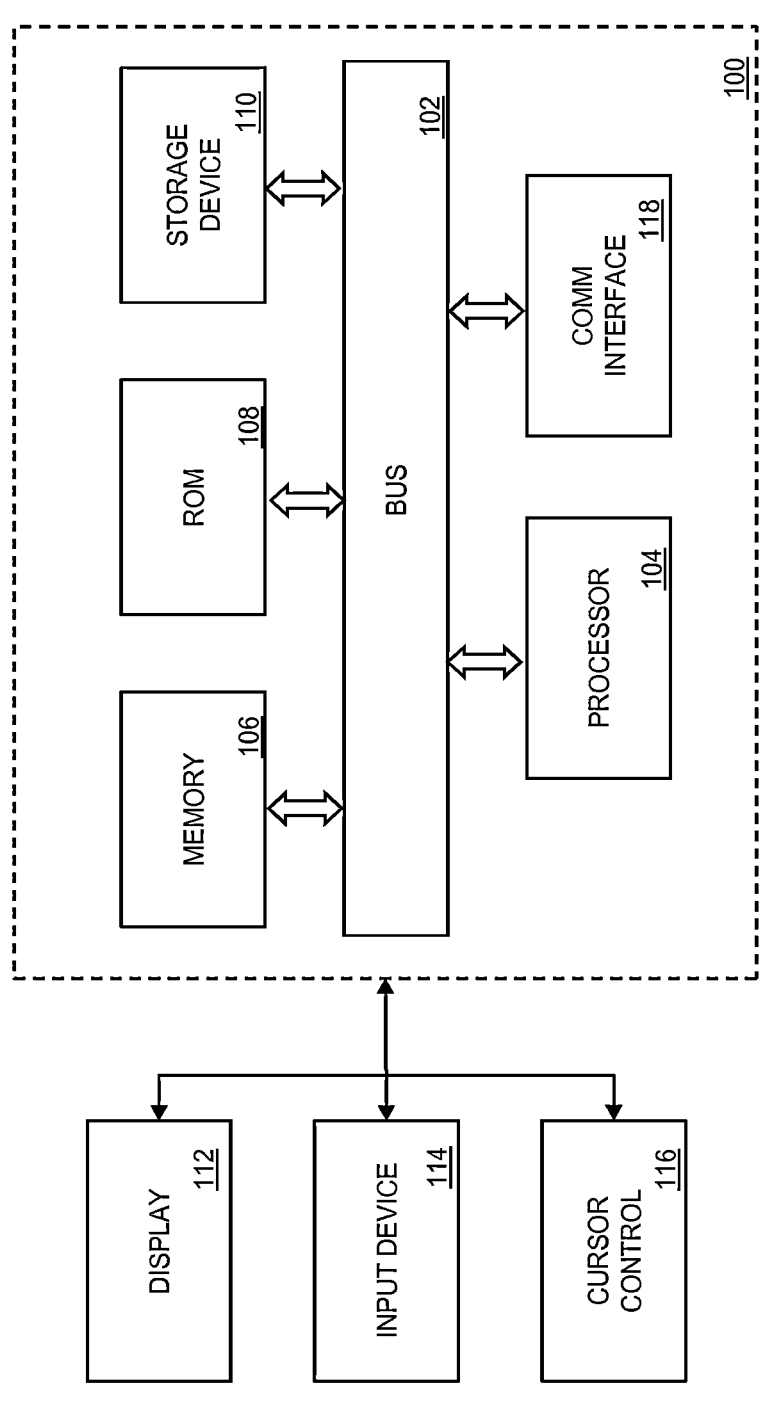
FIG. 1 illustrates an exemplary computing system that various embodiments described herein may be implemented.

FIG. 1 is a block diagram that illustrates a computer system 100 that may be employed to carry out processing functionality, according to various embodiments, upon which embodiments of a thermal cycler system (not shown) may utilize. Computing system 100 can include one or more processors, such as a processor 104. Processor 104 can be implemented using a general or special purpose processing engine such as, for example, a microprocessor, controller or other control logic. In this example, processor 104 is connected to a bus 102 or other communication medium.

Further, it should be appreciated that a computing system 100 of FIG. 1 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 100 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art.

Computing system 100 may include bus 102 or other communication mechanism for communicating information, and processor 104 coupled with bus 102 for processing information.

Computing system 100 also includes a memory 106, which can be a random access memory (RAM) or other dynamic memory, coupled to bus 102 for storing instructions to be executed by processor 104. Memory 106 also may be used for storing temporary variables or other intermediate information during execution of instructions to be executed by processor 104. Computing system 100 further includes a read only memory (ROM) 108 or other static storage device coupled to bus 102 for storing static information and instructions for processor 104.

Computing system 100 may also include a storage device 110, such as a magnetic disk, optical disk, or solid state drive (SSD) is provided and coupled to bus 102 for storing information and instructions. Storage device 110 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 110 may include other similar instrumentalities for allowing computer programs or other instructions or data to be loaded into computing system 100. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 110 to computing system 100.

Computing system 100 can also include a communications interface 118. Communications interface 118 can be used to allow software and data to be transferred between computing system 100 and external devices. Examples of communications interface 118 can include a modem, a network interface (such as an Ethernet or other NIC card), a communications port (such as for example, a USB port, a RS-232C serial port), a PCMCIA slot and card, Bluetooth, etc. Software and data transferred via communications interface 118 are in the form of signals which can be electronic, electromagnetic, optical or other signals capable of being received by communications interface 118. These signals may be transmitted and received by communications interface 118 via a channel such as a wireless medium, wire or cable, fiber optics, or other communications medium. Some examples of a channel include a phone line, a cellular phone link, an RF link, a network interface, a local or wide area network, and other communications channels.

Computing system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104, for example. An input device may also be a display, such as an LCD display, configured with touchscreen input capabilities. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (e.g., x) and a second axis (e.g., y), that allows the device to specify positions in a plane. A computing system 100 provides data processing and provides a level of confidence for such data. Consistent with certain implementations of embodiments of the present teachings, data processing and confidence values are provided by computing system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 104 for execution. Such instructions, generally referred to as "computer program code" (which may be grouped in the form of computer programs or other groupings), when executed, enable the computing system 100 to perform features or functions of embodiments of the present invention. These and other forms of computer-readable media may take many forms, including but not limited to, non-volatile media, volatile media, and transmission media. Non-volatile media includes, for example, solid state, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 104 for execution. For example, the instructions may initially be carried on magnetic disk of a remote computer. The remote computer can load the instructions into its dynamic memory and send the instructions over a telephone line using a modem. A modem local to computing system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

In various embodiments, the devices, instruments, systems, and methods described herein may be used to detect one or more types of biological components of interest. These biological components of interest may be any suitable biological target including, but are not limited to, DNA sequences (including cell-free DNA), RNA sequences, genes, oligonucleotides, molecules, proteins, biomarkers, cells (e.g., circulating tumor cells), or any other suitable target biomolecule.

In various embodiments, such biological components may be used in conjunction with various PCR, qPCR, and/or dPCR methods and systems in applications such as fetal diagnostics, multiplex dPCR, viral detection and quantification standards, genotyping, sequencing validation, mutation detection, detection of genetically modified organisms, rare allele detection, and copy number variation. Embodiments of the present disclosure are generally directed to devices, instruments, systems, and methods for monitoring or measuring a biological reaction for a large number of small volume samples. As used herein, samples may be referred to as sample volumes, or reactions volumes, for example.

While generally applicable to quantitative polymerase chain reactions (qPCR) where a large number of samples are being processed, it should be recognized that any suitable PCR method may be used in accordance with various embodiments described herein. Suitable PCR methods include, but are not limited to, digital PCR, allele-specific PCR, asymmetric PCR, ligation-mediated PCR, multiplex PCR, nested PCR, qPCR, genome walking, and bridge PCR, for example.

As described below, in accordance with various embodiments described herein, reaction sites may include, but are not limited to, through-holes, wells, indentations, spots, cavities, sample retainment regions, and reaction chambers, for example.

Furthermore, as used herein, thermal cycling may include using a thermal cycler, isothermal amplification, thermal convention, infrared mediated thermal cycling, or helicase dependent amplification, for example. In some embodiments, the chip may be integrated with a built-in heating element. In various embodiments, the chip may be integrated with semiconductors.

According to various embodiments, detection of a target may be, but is not limited to, fluorescence detection, detection of positive or negative ions, pH detection, voltage detection, or current detection, alone or in combination, for example.

Various embodiments described herein are particularly suited for digital PCR (dPCR). In digital PCR, a solution containing a relatively small number of a target polynucleotide or nucleotide sequence may be subdivided into a large number of small test samples, such that each sample generally contains either one molecule of the target nucleotide sequence or none of the target nucleotide sequence. When the samples are subsequently thermally cycled in a PCR protocol, procedure, or experiment, the sample containing the target nucleotide sequence are amplified and produce a positive detection signal, while the samples containing no target nucleotide sequence are not amplified and produce no detection signal. Using Poisson statistics, the number of target nucleotide sequences in the original solution may be correlated to the number of samples producing a positive detection signal.

In order to conduct a typical dPCR protocol, procedure, or experiment, it is advantageous to be able to divide an initial sample solution into tens of thousands or hundreds of thousands of test samples each having a volume of several nanoliters, at or about one nanoliter, or less than one nanoliter, in a way that is simple and cost effective. Because the number of target nucleotide sequences may be very small, it may also be important in such circumstances that the entire content of the initial solution be accounted for and contained in the plurality of reaction sites.

Embodiments described herein solve these and other dPCR design constraints by displaying results from an experiment in a user-friendly and valuable way for a user so that the user may be able evaluate the quality of an experiment as well as determine information about the biological components, as will be described in this document.

Figure 10:
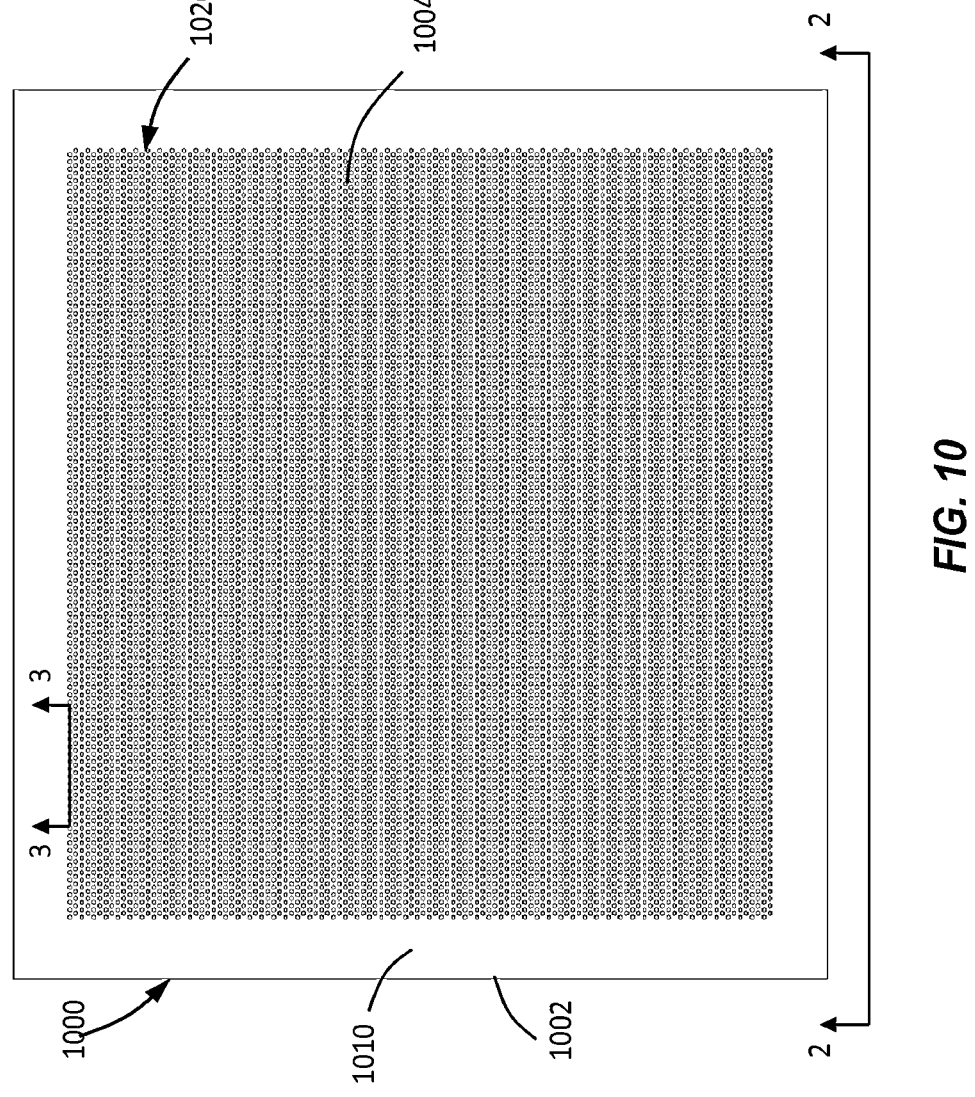
FIG. 10 illustrates a chip including reaction sites where data is gathered from and visualized according to various embodiments described herein.

In various embodiments, the devices, instruments, systems, and methods described herein may be used to detect one or more types of biological components of interest. These biological components of interest may include, but are not limited to, DNA sequences, RNA sequences, genes, oligonucleotides, or cells (e.g., circulating tumor cells). In various embodiments, such biological components may be used in conjunction with various PCR, qPCR, and/or dPCR methods and systems in applications such as fetal diagnostics, multiplex dPCR, viral detection and quantification standards, genotyping, sequencing validation, mutation detection, detection of genetically modified organisms, rare allele detection, and copy number variation. With reference to FIG. 10, in certain embodiments of the present teachings a chip 100 comprises a substrate 1002 and a plurality of reaction sites. Chip 1000 may also be referred to as an article, device, array, slide, or platen, for example.

According to various embodiments of the present disclosure, reaction sites may be, but are not limited to, wells, cavities, indentations, spots, reaction chambers, sample retainment regions, or through-holes, for example, located in substrate 1002. Reaction sites may be any structure that allows a sample to be independent of other samples located on the substrate. Substrate 1002 comprises a first surface 1010 and an opposing second surface 1012.

The reactions sites 1004 are configured to provide sufficient surface tension by capillary action to hold respective liquid samples containing a biological sample to be processed or examined.

Substrate 1002 may be a flat plate or comprise any form suitable for a particular application or design. Substrate may comprise, in total or in part, any of the various materials known in the fabrication arts including, but not limited to, a metal, glass, ceramic, silicon material, or the like. Additionally or alternatively, substrate 1002 may comprise a polymer material such as an acrylic, styrene, polyethylene, polycarbonate, and polypropylene material. Substrate 1002 and reaction sites 1004 may be formed by one or more of machining, injection molding, hot embossing, laser drilling, photolithography, or the like.

Figure 2:
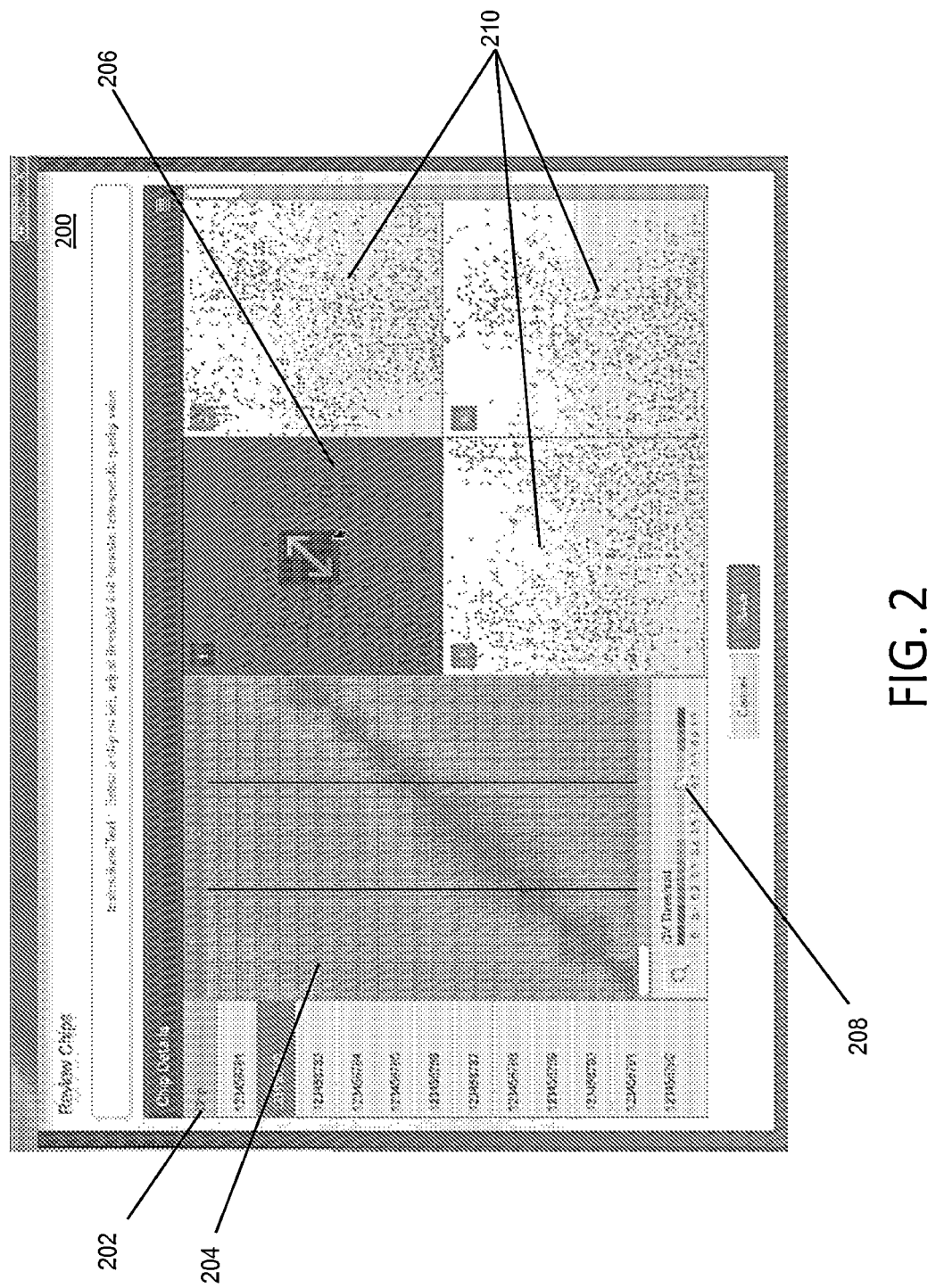
FIG. 2 illustrates a data visualization according to various embodiments described herein.

FIG. 2 illustrates a graphical user interface (GUI) 200 for a display showing various data visualizations to a user. GUI 200 provides data visualizations to the user from an experiment performed on a chip so the user may review the data. According to various embodiments described herein, to help a user identify data for further analysis based on quality, for example, different data visualizations may be generated by a processor for displaying to a user. According to various embodiments, the data includes detected fluorescence data from each of the plurality of reaction sites. GUI 200 may allow a user to select a chip whose data the user wishes to view. GUI 200 may display data from at least one experiment. In the example shown in FIG. 2, data from several different chips are displayed on GUI 200 for a user. The available chip data may be displayed in menu 202 for a user to select. When a user selects a chip to view, the corresponding data may be displayed in various ways so that a user may identify the positive and negative reactions in the plurality of reactions sites. In other words, the positive reactions (fluorescence detected) in a reaction site will be displayed in one color while the negative reactions (no fluorescence detected) in a reaction site will be displayed in a second color.

Further, a user viewing representations of the positive and negative reactions and positions of positive and negative reactions may be able to better identify any errors or aberrations in the data or in the experiment. For example, insufficient loading of the sample into a plurality of reaction sites in one portion of the chip may be obvious from a data visualization of the chip. Because of the large number of reaction sites in a chip, to be able to usefully view the positive and negative reactions, the chip may visualized in a plurality of portion views. In this way, the user may be able to view a display of positive and negative reactions in smaller portions for ease of viewing. For example, a first quadrant of data 206 may be selected by the user to view. The data from three other quadrants of the chip 210 may be available to view when the user selects them.

Figure 3:
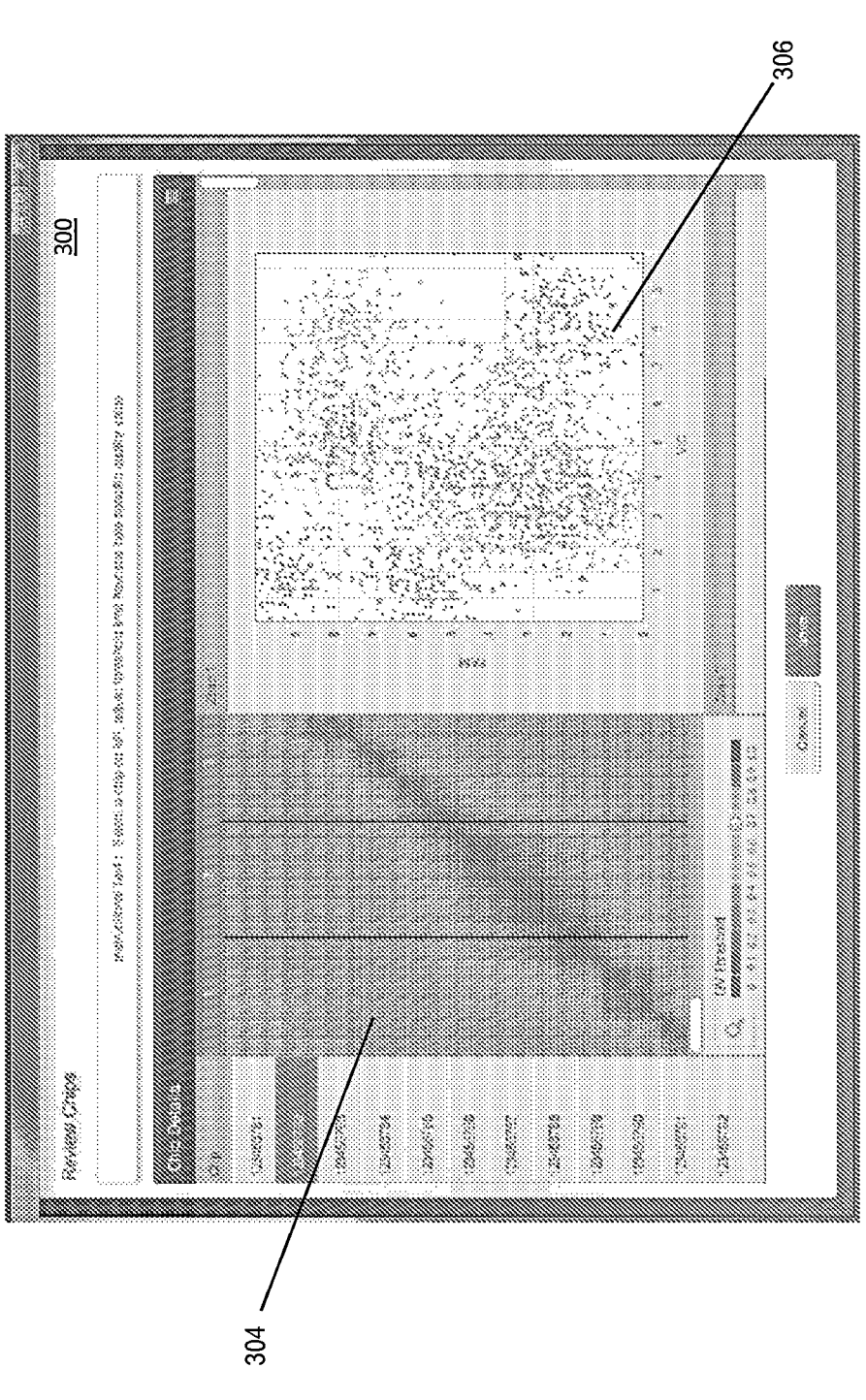
FIG. 3 illustrates a data visualization according to various embodiments described herein.

For example, FIG. 3 illustrates a representation 306 of a selected portion of a chip. In this representation, positive and negative reaction sites may be displayed. Further, the positive reaction sites for a plurality of fluorescent dyes may be displayed. In representation 306, both FAM and VIC positive reaction sites are displayed.

In various embodiments described herein, a user may also desire to view the quality of data from the plurality of reaction sites. The quality value may be used to measure the degree to which data values from a given reaction site can be trusted as reliable or accurate data. With reference to FIG. 2, in GUI 200, a heatmap 204 illustrating the data quality of the detected emission data may be generated for a user so that a user may see where the quality of data may be good or poor. In various embodiments, data quality may be based on detected intensity, for example. Data quality may also be based on determining characteristics of the detected data from reaction sites around the reaction site where the data quality is being determined. For example, if there is a large number of positive reactions sites surrounding a particular reaction site, the data from the particular reaction site may be determined to be of a low quality because the experimental setup is not expected to generate such a high density of positive reactions. This may be due to bridging of a sample across reaction sites or an error when loading the sample to the reaction sites, for example. Methods of determining data quality may be found in application Nos. 61/803,028 and 61/827,483 (LT00800 PRO and LT00800 PRO 2), for example.

A user may be able to select a threshold using slider 208. A threshold allows a user to select data points meeting or exceeding a desired threshold. The data points displayed may be only the points that meet or exceed the desired quality threshold. Further, data may be selected for further analysis based on determined quality. Additionally, other plots may be generated based on a selected threshold such as scatter plots or histograms.

Figure 4:
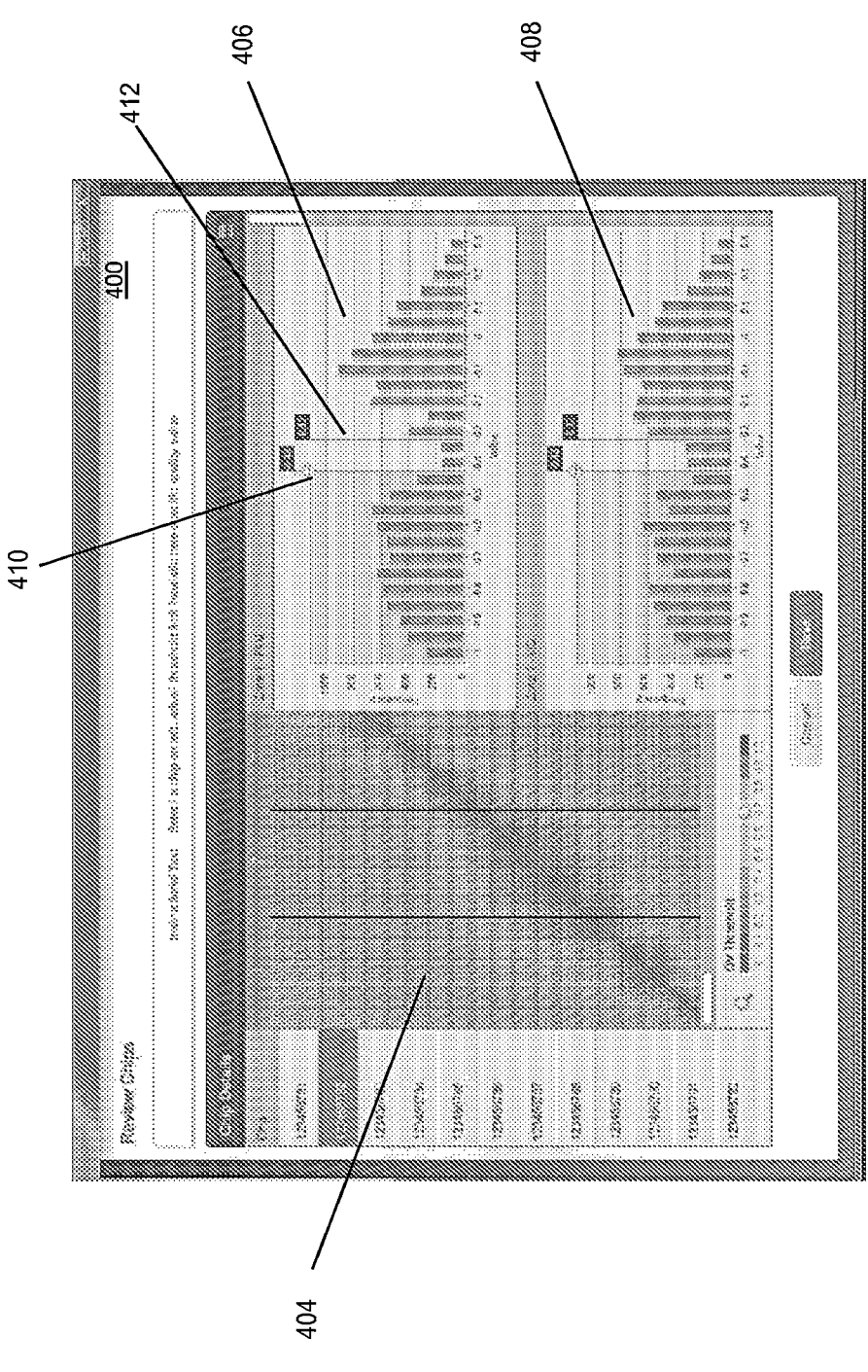
FIG. 4 illustrates a data visualization according to various embodiments described herein.

In addition to FIG. 2, FIGS. 3 and 4 illustrate various methods and displays for viewing a zone, or portion, of a chip including reactions sites and associated quality values of data.

FIG. 4 illustrates a histogram of the plurality of data points of the reaction sites. According to various embodiments, histograms 406 and 408 may be generated by determining quality values for the emission data from a chip. Histograms 406 and 408 allow a user to visualize the frequency of reaction sites at a certain quality level. In this way, a user may be able to determine if the quality value threshold they selected is a good threshold to set based on the number of data points at a certain quality value.

Histogram 406 may be displayed to a user. On histogram 406, an indicator 410 showing an automatic threshold determined by a processor may be displayed. Further, a user may also have the ability to manually select a threshold using indicator 412. The data values used in generating histogram 406 may be selected by setting a threshold for quality value as described above. Additionally, according to various embodiments, a histogram may generated by weighting fluorescence values with the quality values.

By displaying heatmap 404 along with histogram 406 and 408, a user can easily determine how changing the threshold for quality value affects the data and subsequent analysis.

Figure 5:
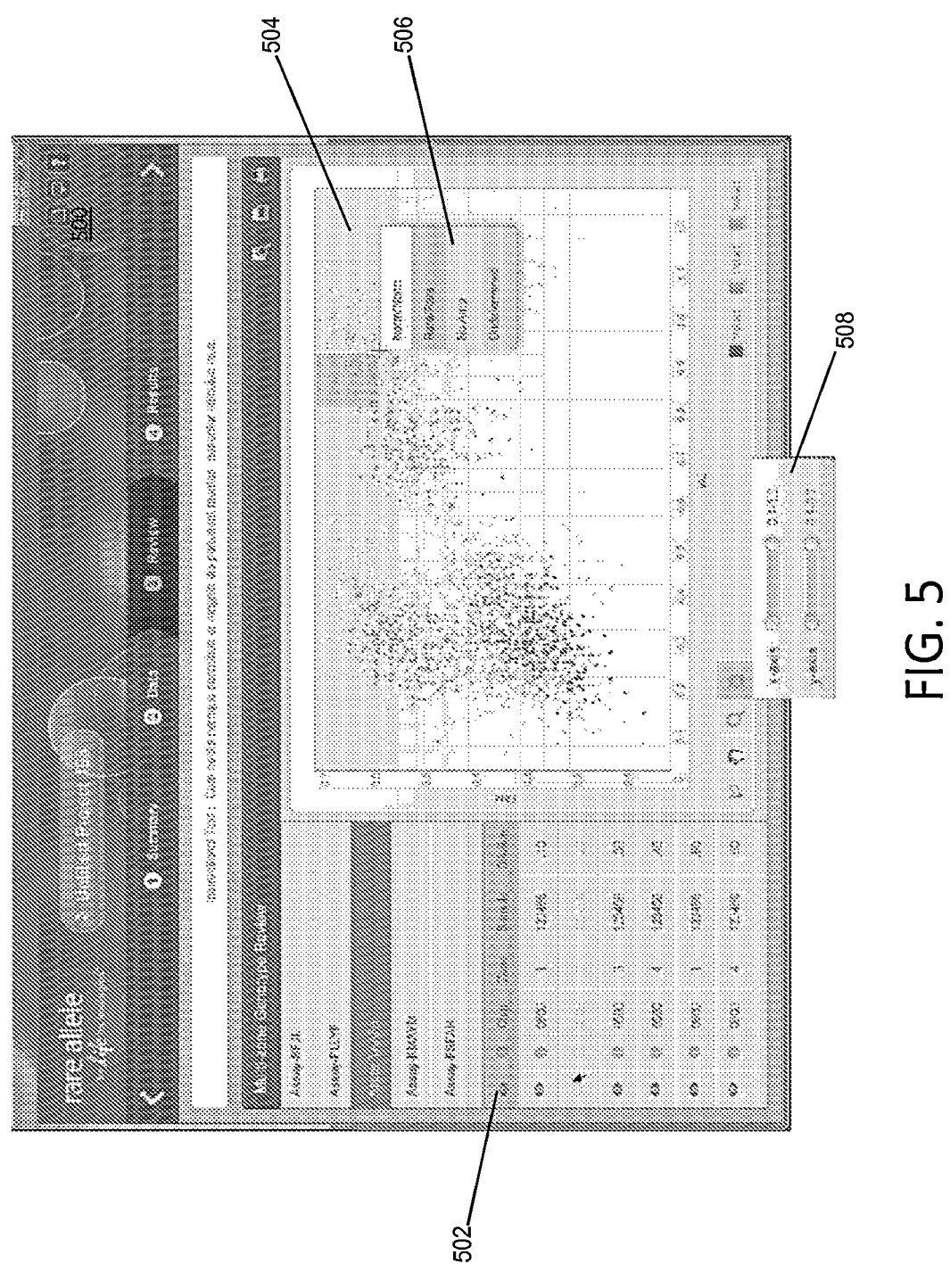
FIG. 5 illustrates a data visualization according to various embodiments described herein.

FIG. 5 illustrates GUI 500 including a point density plot 504 according to various embodiments described herein. Point density plot 504 is a plot of detected florescent values of one fluorescent label versus another fluorescent label. In this example, FAM emission values are plotted against VIC emission values for each reaction site. In this way, the density of data values may be visualized.

Furthermore, GUI 500 includes data table 502 showing more information for data points selected and displayed in scatter plot 504. Since the number of data values associated with an assay may be very large, sometimes millions of points, the scatter plot may only display a portion of the data points. The details associated with the selected data points in scatter plot 504 may be viewable in data table 502. A processor may use a whole set of data to generate a complete scatter plot. However, various portions of the data may be selected by the user to be displayed on GUI 500.

In other embodiments, a smooth scatter plot view (not shown) may be generated instead of a density view.

Further, scatter plot 504 may be used as a principal axis tool. According to various embodiments, a principal axis tool allows the user to place one or more pairs of axes on the scatter plot and rotate these axes to align with the data.

Figure 6:
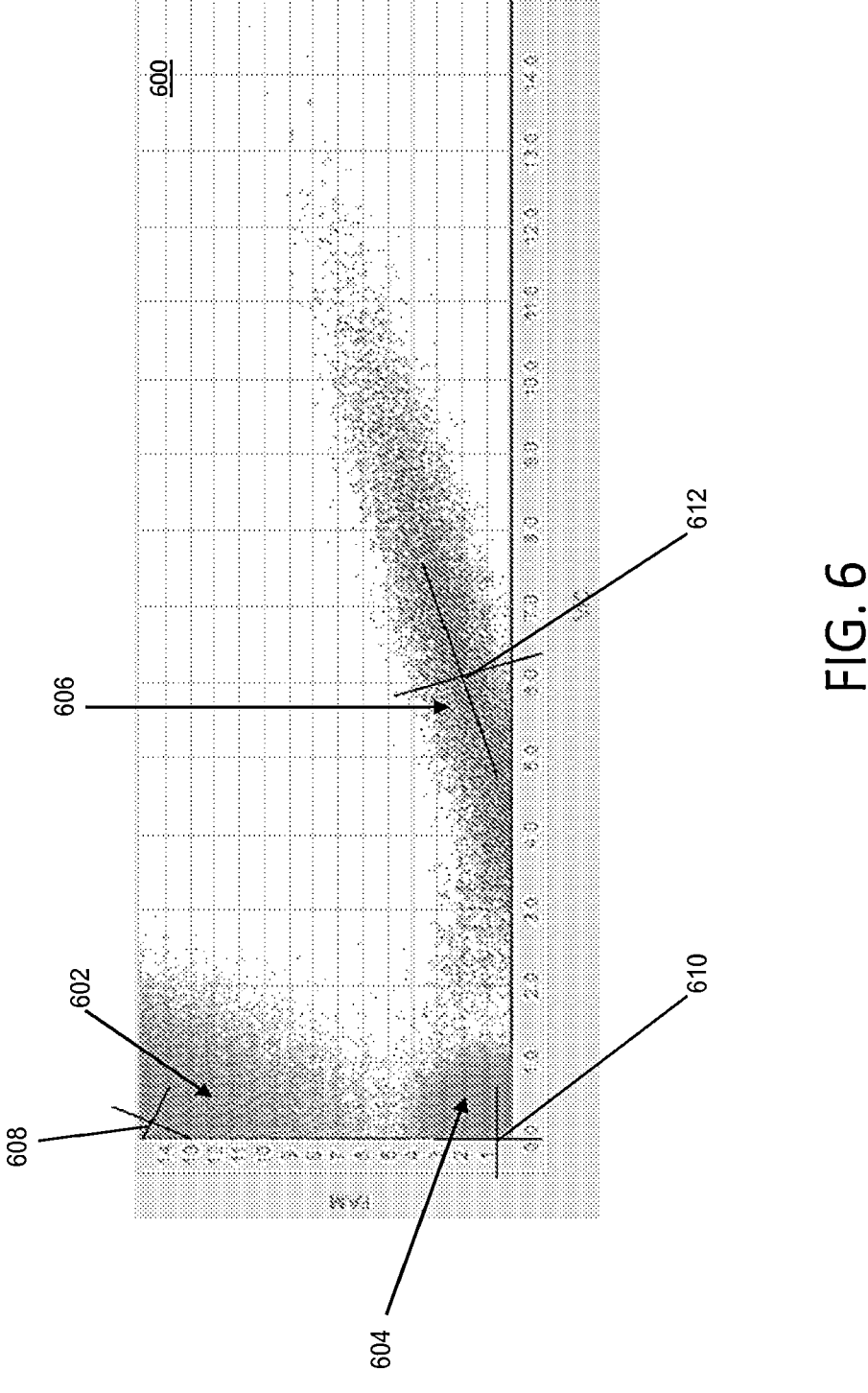
FIG. 6 illustrates a generated plot to visualize data according to various embodiments described herein.

For example, in FIG. 6, the user has placed three principal axes within high density areas in scatter plot 600. Scatter plot 600 shows FAM v. VIC positive reaction calls. There are three high density areas 602, 604, and 606. In each of these high density areas, a principal axis is displayed on GUI 600. Principal axis 608 is displayed in high density area 602. Principal axis 610 is displayed in high density area 604. Principal axis 612 is displayed in high density area 612. The origin of the axes is placed at or close to the center of mass of a cluster of points. The axes are lined up with the major and minor axes of the cluster of points (assumed to be roughly ellipsoidal). These axes can be used as guides to better identify subset membership of points. Simple algorithms may be used to determine cluster membership such as searching along a given axis to find when point density has decreased to a target level or computing the variation of the data along each axis and including points that fall within a specified number of standard deviations from the center of mass.

In other embodiments, other methods for placing guides to determine cluster membership such as drawing dividing lines between the clusters may be used.

Figure 7:
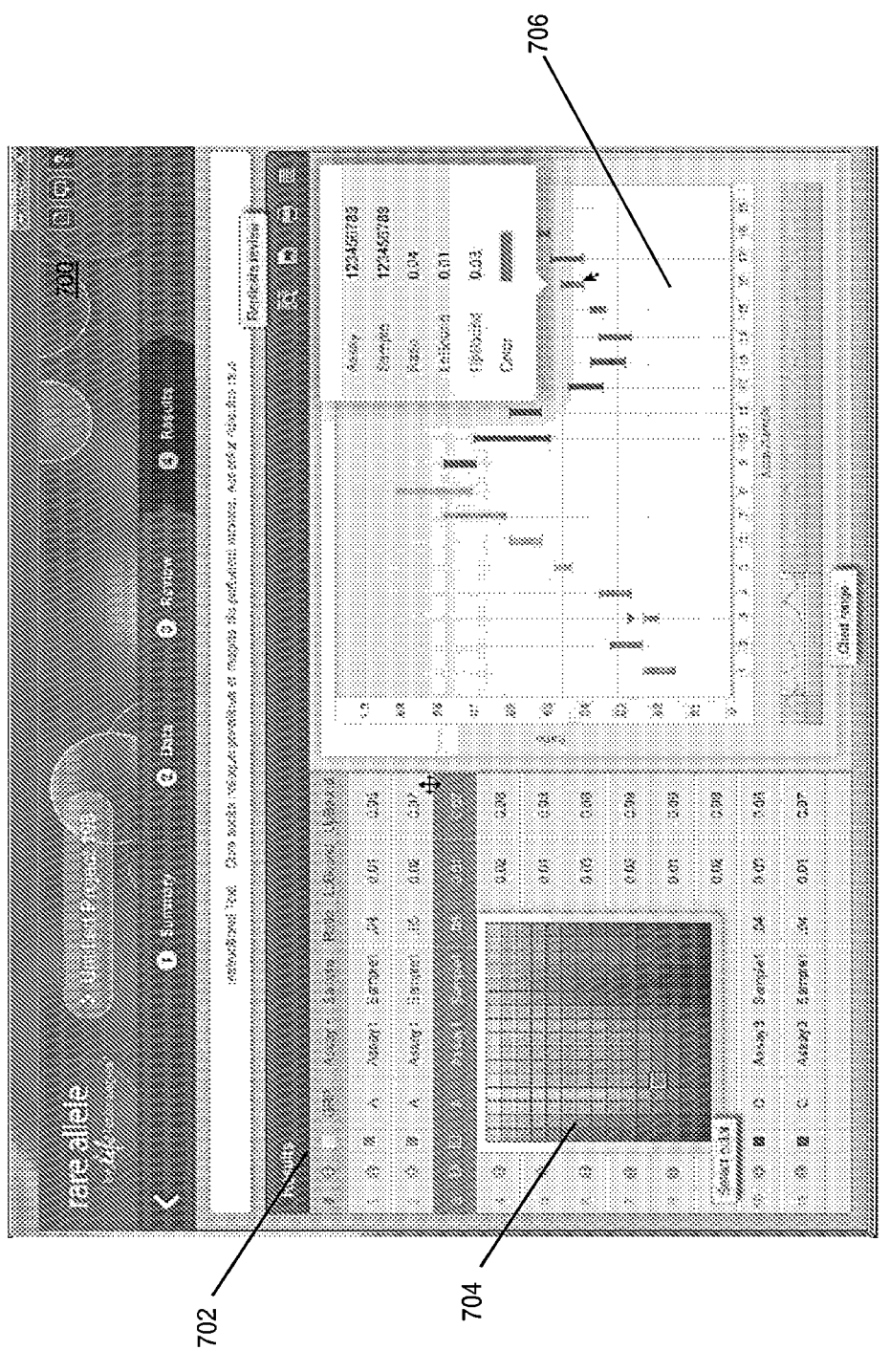
FIG. 7 illustrates a generated plot to visualize data according to various embodiments described herein.

FIG. 7 illustrates another way to represent a large quantity of data alongside context information. Plot 706 shows a plurality of assays and associated range of ratios of detected emission data. Data table 702 may also show information associated with a plurality of different samples/assays displayed in plot 706. Data table 702 may be sorted in a plurality of ways. In this example, each point on plot 702 is a row of data table 702. Furthermore, according to various embodiments, rows of data table 702 may be color coded by a user using tool box 704 so that the corresponding points in plot 706 are also labeled with the selected color for easy identification. A user selects a color from tool box 704 to associate a color to a row in data table 702 corresponding to data from a certain assay/sample.

Figure 8:
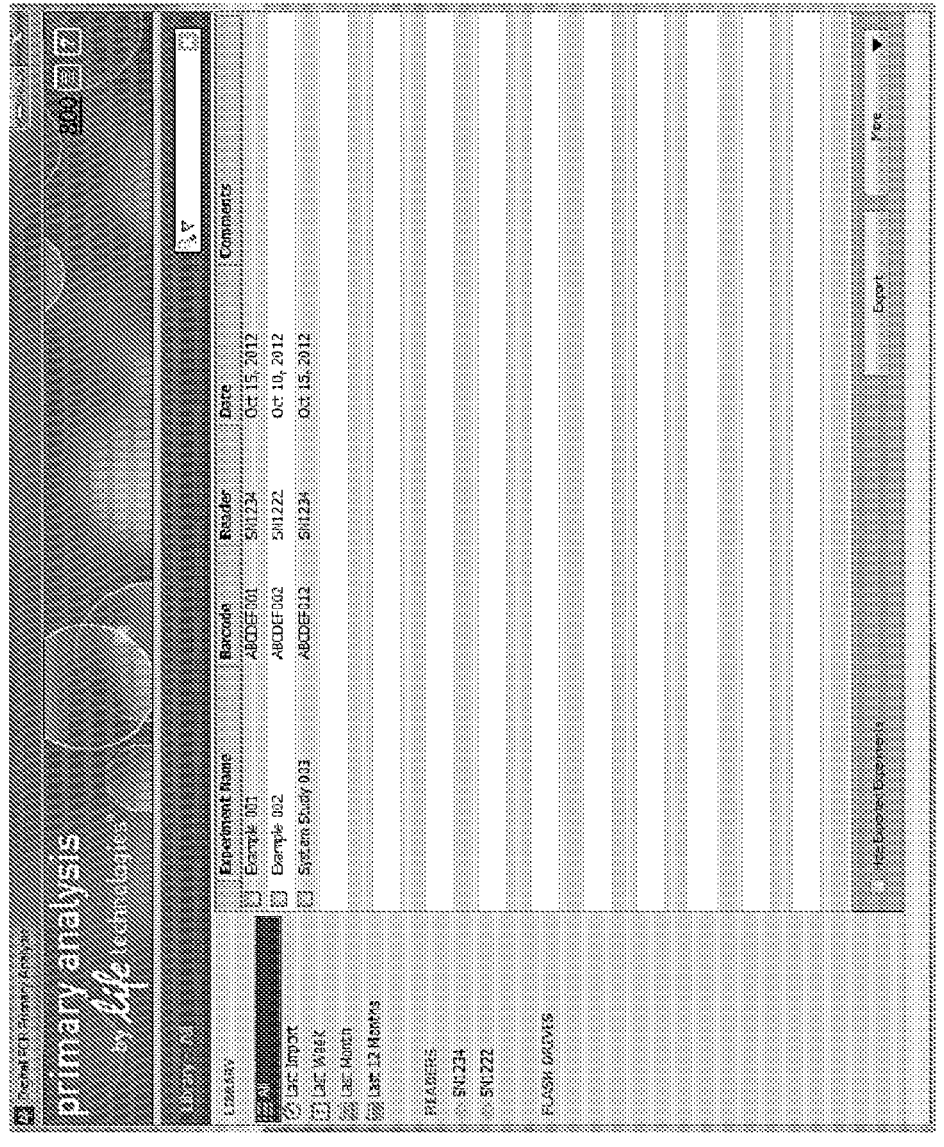
FIG. 8 illustrates a tool for organizing experiments according to embodiments described herein.

FIG. 8 illustrates GUI 800 showing various experiment data that a user may store after performing a plurality of reactions according to various embodiments described herein. The user may then select an experiment to view and analyze the data associated with an experiment. Information such as the experiment name, barcode identifier on the chip used, the reader used for emission detection, and the date the experiment was performed may also be displayed, for example.

Figure 9:
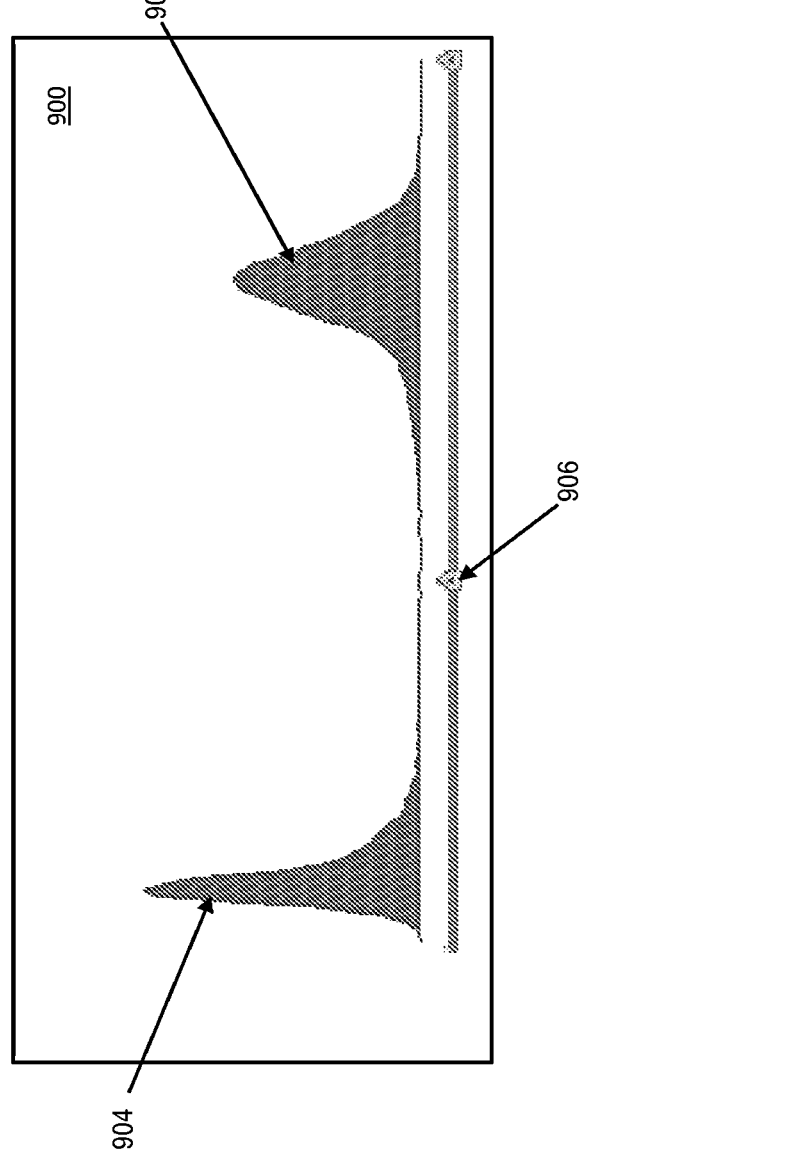
FIG. 9 illustrates a histogram of fluorescent values from a plurality of data points according to various embodiments described herein.

FIG. 9 shows a histogram that may be generated based on fluorescent emission values to assist a user in distinguishing positive versus negative reactions. A user may adjust the threshold for counting data values as positive versus negative according to various embodiments. GUI 900 is displayed to a user on a display screen. The user can visualize the fluorescent emission data values in a histogram view. The example in FIG. 9 illustrates 2 peaks, 904 and 902. GUI

900 shows data values that were binned at a higher fluorescent intensity value in peak 902. GUI 900 also shows data values that were binned at a lower fluorescent intensity value in peak 904. The user may be able to change the threshold value with slider 906 that the processor will use to distinguish a positive reaction site from a negative reaction site. In this example, all the data emission values to the left of slider 906 will be identified as negative reaction sites by the processor, and the data emission values to the right of slider 906 as positive reaction sites. These values are used in further analysis. A user may recognize that a cluster of emission data values should be identified as positive reaction sites when the processor had previously determined the same reaction sites as negative reaction sites. As such, the user may adjust the threshold to adjust positive/negative determination results, which may affect further analysis by the user. In this way, the user can improve their analysis results from a visual inspection of the data.

Figure 11:
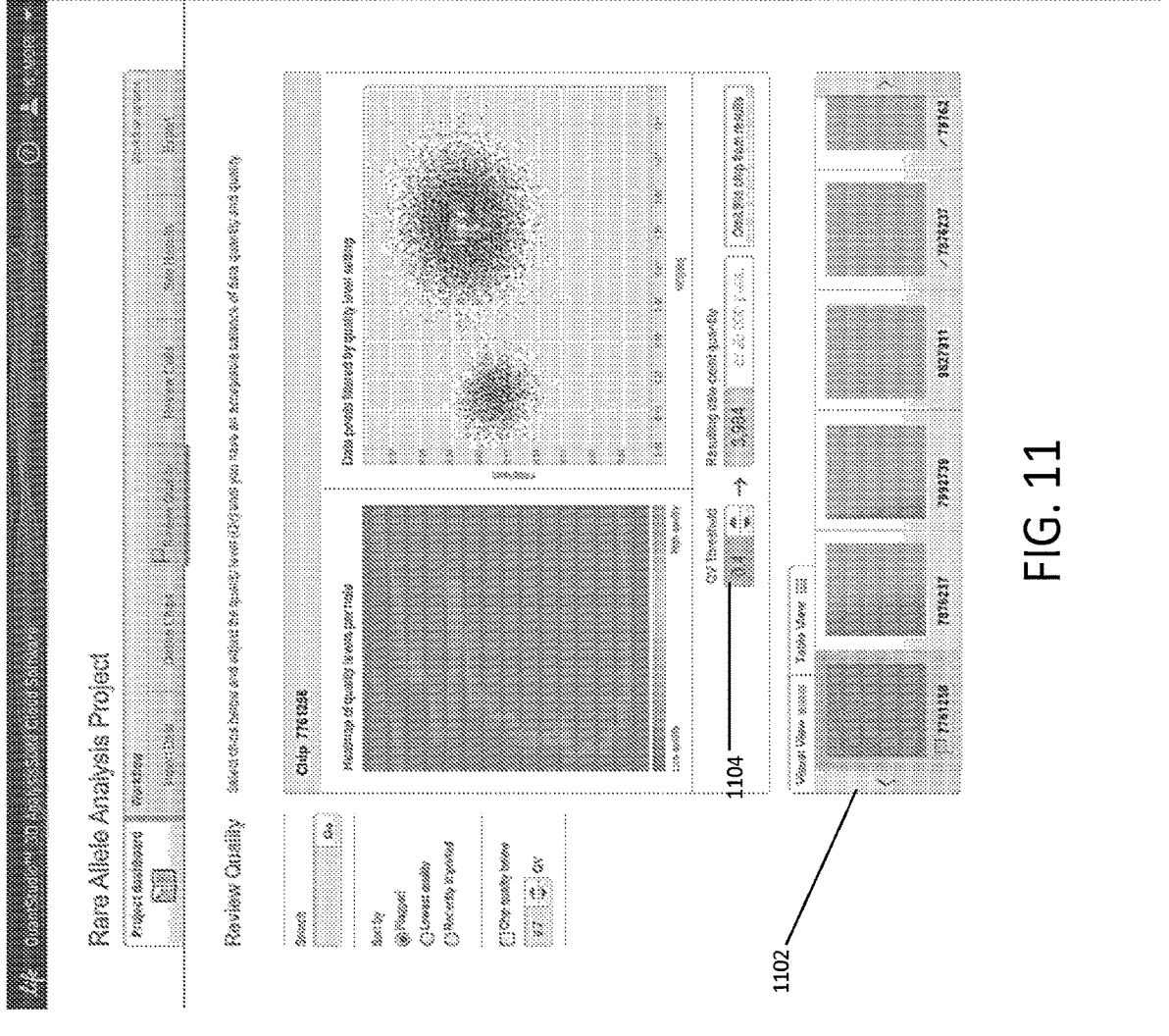
FIG. 11 illustrates a tool for reviewing data according to various embodiments described herein.

FIG. 11 illustrates a tool a user may use to adjust the data for analysis based on the data results from a biological reaction. For example, a user may notice the quality of the data for a set of reactions may be low and wish to filter the low quality data out of the analysis for the overall results of an experiment. Low quality data may occur by contamination, bridging of liquid sample between reaction sites, or optical errors, for example. A user may adjust the quality value threshold to filter the data with user control 1104 in various embodiments. A user may be able to visualize the quality of data across the chip with a data visualization such as heatmap 1106. In heatmap 1106, data determined to be of low quality is displayed as a different color than data of higher quality.

A user may also visualize data by thumbnail images 1102. Thumbnail images 1102 may illustrate data results from the biological reactions of other chips. In this way, a user may be able to visualize the data results in order to determine overall quality of data or determine if certain results should be omitted from the overall analysis for the experiment. A user may toggle between a visual view with the thumbnails 1102 or view the data results in a table format.

Figure 12:
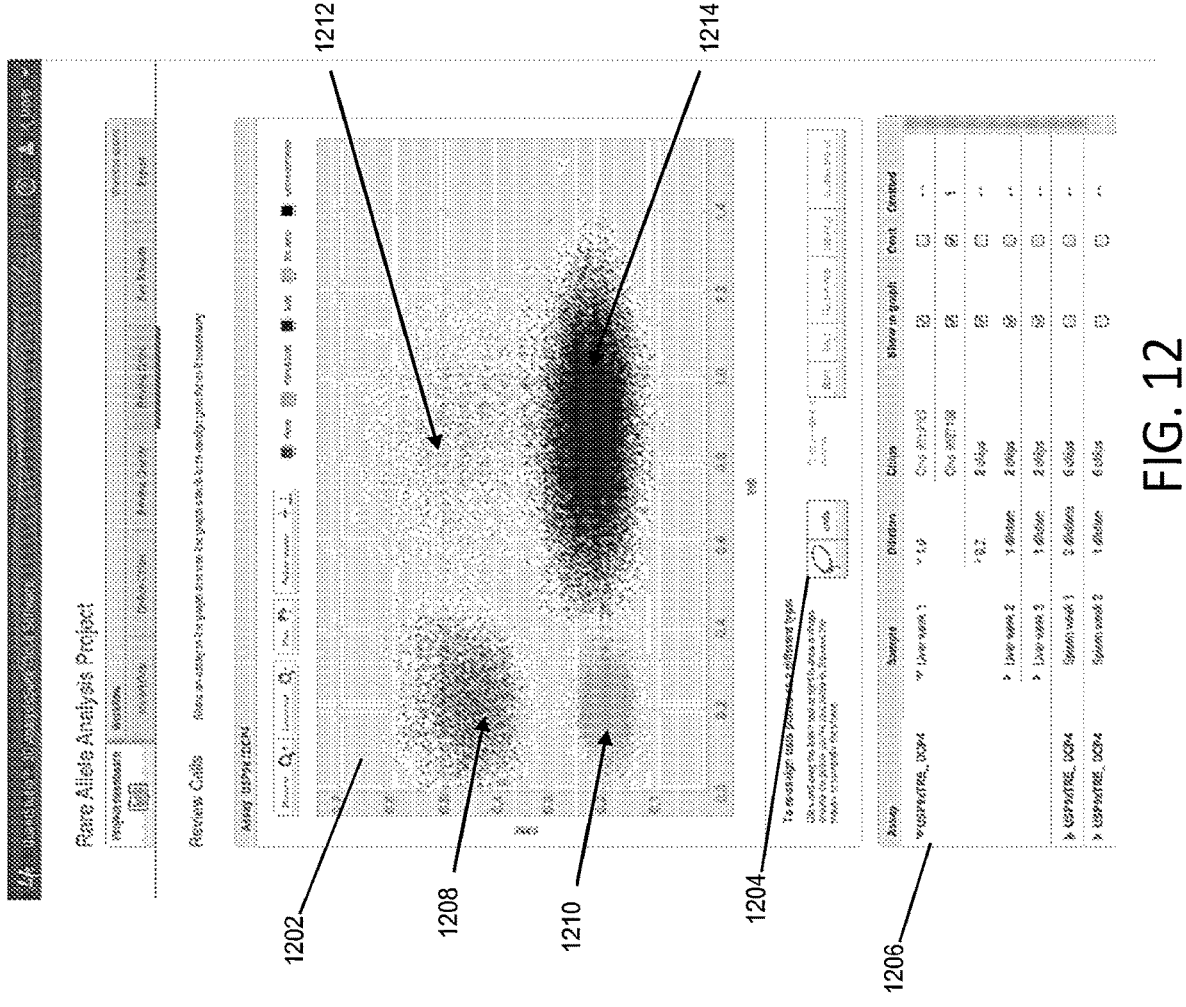
FIG. 12 illustrates a tool for adjusting and organizing data according to various embodiments described herein.

FIG. 12 illustrates another data visualization tool according to embodiments of the present teachings. Although a processor may automatically classify data based on a predetermined threshold or a calculated threshold, a user may recognize that data should be reclassified based on experience or pattern recognition, for example. The classification of data may affect the overall results from the experiment so a user may desire reclassifying data if she believes there is a more accurate classification for specific data points after visualizing the data points on plot 1201, for example. Thus, a user may adjust the classification of specific data points by using tool 1204, for example. Using tool 1204, the user may select a group of data points she wishes to reclassify. For example, the use may reclassify data points classified as "rare" to "no-amplification." A user may select the points using tool 1204 and change the data classification. In other embodiments, a user may be able to click on individual data points and adjust the point's classification.

In the example illustrated in FIG. 12, plot 1201 displays 4 main clusters of data points, cluster 1208, cluster 1210, cluster 1212, and cluster 1214. In this example, two different fluorescent dyes, FAM and VIC, were used to identify molecules. Cluster 1208 represents data points that were classified as including FAM dye. Cluster 1210 represents data points that were classified as having no amplification. Cluster 1212 represents data points that were classified as having both FAM and VIC dyes. Cluster 1214 represents data points that were classified as including VIC dye. Upon visual inspection of plot 1201, a user may see that some data points, not within the main cluster were classified by the processor in a certain category. The user, however, determines that the data point should be classified within another category. For example, a user may see some data points classified as including FAM dye when the user believes that those data points should be classified as including both FAM and VIC dye. According to various embodiments, the user may select those data points and change the classification. According to various embodiments, classifications may include, but are not limited to, the type of fluorescent dye detection, like FAM and VIC, no amplification, or undetermined, for example. A user may select the data points to change classification by clicking on an individual data point or by selecting a group of data points with tool 1204, for example. As a result, the processor than uses the adjusted number of data points to calculate results, such as concentration of a molecule within the sample or copy number. As described above, based on the Poisson algorithm and the number of positive and negative reaction sites, the number of molecules of interest may be determined.

According to various embodiments, plot 1202 is a data visualization that helps a user make a determination about the nature and quality of the data from their experiment. Plot 1202 also allows a user to make adjustments to classification of data In yet other embodiments, a user may use a classification tool to select all the points she believes should be a particular classification that were not originally classified that way by the system. For example, a user may wish to re-classify several points as "wild" type. A user may select a wild-type classification tool and then select all the points she believes should be reclassified as "wild." The data points will be adjusted to reflect the new classification, such as by changing color on plot 1202.

Further, according to various embodiments, a summary of various assays 1206 may be accessed by the user. A user may access a nested hierarchy of information that will indicate various levels of information a user may choose to view. A user may be initially offered a high overview of assay data available and may choose to view more details of an assay. For example, as shown in summary 1206, a use may select the first assay. The view may change so that the user may view the different samples that were used with the first assay. In this example, three samples, Liver week 1, Liver week 2, and Liver week 3, may be viewed by the user. Further, the user may then choose to expand the viewed data for a sample to view the different dilutions used with a particular sample. In this example, two dilutions were used with the Liver week 1 sample. The user may also view the chip used to run a particular dilution and also have a choice as to whether this particular data is shown on the visualization 1202.

Although the present invention has been described with respect to certain exemplary embodiments, examples, and applications, it will be apparent to those skilled in the art that various modifications and changes may be made without departing from the invention.

What is claimed is:

1. A method for generating a data visualization of data obtained from a biological sample analysis, the method comprising:

displaying, at a display comprising a graphical user interface, a scatter plot of data points corresponding to detected data from a plurality of sites of a substrate containing sample subjected to a biological analysis assay, the detected data comprising fluorescence emission intensity emitted from a plurality of dyes, wherein:

axes of the scatter plot correspond respectively to a first fluorescence emission intensity corresponding to a first dye of the plurality of dyes as a label for first amplified product of a first template nucleic acid, and to a second fluorescence emission intensity corresponding to a second dye of the plurality of dyes as a label for a second amplified product of a second template nucleic acid;

indicating, with a first indicator, a first cluster of data points of the scatter plot, the first cluster of data points corresponding to a first set of the plurality of sites classified as having no amplified product detected based on the detected fluorescence emission intensity;

indicating, with a second indicator, a second cluster of data points of the scatter plot, the second cluster of data points corresponding to a second set of the plurality of sites classified as having the first amplified product detected based on the detected fluorescence emission intensity;

indicating, with a third indicator, a third cluster of data points of the scatter plot, the third cluster of data points corresponding to a third set of the plurality of sites classified as having the second amplified product detected based on the detected fluorescence emission intensity; and indicating, with a fourth indicator, a fourth cluster of data points of the scatter plot, the fourth cluster of data points corresponding to a fourth set of the plurality of sites classified as having both the first amplified product and the second amplified product detected based on the detected fluorescence emission intensity, wherein the first, second, third, and fourth indicators differ from each other.

2. The method of claim 1, wherein the plurality of sites is at least 20,000 sites.

3. The method of claim 1, wherein the biological analysis assay is a digital polymerase chain reaction assay.

4. The method of claim 1, wherein the first dye and the second dye differ from each other.

5. The method of claim 1, wherein the first template nucleic acid and the second template nucleic acid differ from each other.

6. The method of claim 1, further comprising indicating, with one or more additional indicators, one or more additional clusters of data points of the scatter plot corresponding to detected fluorescence emission intensity data from one or more sets of a plurality of sites from a second substrate containing sample subjected to a biological analysis assay.

7. The method of claim 1, further comprising reclassifying, based on user input, one or more data points of the first, second, third, or fourth clusters to another of the first, second, third, or fourth clusters or to a new classification not corresponding to a classification associated with the first, second, third, or fourth clusters.

8. The method of claim 7, wherein the user input comprises selection of the one or more data points using a selection tool of the graphical user interface.

9. The method of claim 8, wherein the selection tool comprises a tool configured to allow selection of a group of data points.

10. The method of claim 8, wherein the selection tool comprises a tool configured to allow selection of individual data points.

11. A system for analysis of biological assay data, the system comprising:

a processor; and a memory encoded with instructions to:

display on a display comprising a graphical user interface, a scatter plot of data points corresponding to detected data from a plurality of sites of a substrate containing sample subjected to a biological analysis assay, the detected data comprising fluorescence emission intensity emitted from a plurality of dyes, wherein:

axes of the scatter plot correspond respectively to a first fluorescence emission intensity corresponding to a first dye of the plurality of dyes as a label for first amplified product of a first template nucleic acid, and to a second fluorescence emission intensity corresponding to a second dye of the plurality of dyes as a label for a second amplified product of a second template nucleic acid, indicate, with a first indicator, a first cluster of data points of the scatter plot, the first cluster of data points corresponding to a first set of the plurality of sites classified as having no amplified product detected based on the detected fluorescence emission intensity;

indicate, with a second indicator, a second cluster of data points of the scatter plot, the second cluster of data points corresponding to a second set of the plurality of sites classified as having the first amplified product detected based on the detected fluorescence emission intensity;

indicate, with a third indicator, a third cluster of data points of the scatter plot, the third cluster of data points corresponding to a third set of the plurality of sites classified as having the second amplified product detected based on the detected fluorescence emission intensity; and indicate, with a fourth indicator, a fourth cluster of data points of the scatter plot, the fourth cluster of data points corresponding to a fourth set of the plurality of sites classified as having both the first amplified product and the second amplified product detected based on the detected fluorescence emission intensity, wherein the first, second, third, and fourth indicators differ from each other.

12. The system of claim 11, wherein the memory is further encoded with instructions to:

indicate, with one or more additional indicators, one or more additional clusters of data points of the scatter plot corresponding to detected fluorescence emission intensity data from one or more sets of a plurality of sites from a second substrate containing sample subjected to a biological analysis assay.

13. The system of claim 11, wherein the biological analysis assay is a digital polymerase chain reaction assay.

14. The system of claim 11, wherein the first dye and the second dye differ from each other.

15. The system of claim 11, wherein the first template nucleic acid and the second template nucleic acid differ from each other.

16. The system of claim 11, wherein the memory is further encoded with instructions to:

reclassify, based on user input, one or more data points of the first, second, third, or fourth clusters to another of the first, second, third, or fourth clusters or to a new classification not corresponding to a classification associated with the first, second, third, or fourth clusters.

17. The system of claim 16, wherein the user input comprises selection of the one or more data points using a selection tool of the graphical user interface.

18. The system of claim 17, wherein the selection tool comprises a tool configured to allow selection of a group of data points.

19. The system of claim 17, wherein the selection tool comprises a tool configured to allow selection of individual data points.

\*   \*   \*   \*   \*